United States Patent
Baba et al.

[11] Patent Number: 6,123,943
[45] Date of Patent: Sep. 26, 2000

[54] NF-KB ACTIVITY INHIBITOR

[75] Inventors: Masanori Baba, Kagoshima; Minoru Ono, Tokyo, both of Japan

[73] Assignee: Kaken Shoyaku Co., Ltd., Tokyo, Japan

[21] Appl. No.: 09/037,712

[22] Filed: Mar. 10, 1998

[30] Foreign Application Priority Data

Dec. 22, 1997 [JP] Japan ..................................... 9-353879

[51] Int. Cl.$^7$ ................................................... A61K 35/78
[52] U.S. Cl. ........................ 424/195.1; 514/308; 514/387; 514/415
[58] Field of Search ......................... 424/195.1; 514/387, 514/308, 415; 546/140, 139; 534/790

[56] References Cited

U.S. PATENT DOCUMENTS

| | | | |
|---|---|---|---|
| 5,025,020 | 6/1991 | Van Dyke | 514/280 |
| 5,534,523 | 7/1996 | Ono et al. | 514/308 |
| 5,627,195 | 5/1997 | Hu | 514/321 |
| 5,641,773 | 6/1997 | Pardee et al. | 514/221 |

FOREIGN PATENT DOCUMENTS

| | | | |
|---|---|---|---|
| 0 476 391 A2 | 3/1992 | European Pat. Off. | A61K 31/47 |
| 1-233220 | 9/1989 | Japan . | |
| 8-301761 | 11/1996 | Japan | A61K 31/47 |

OTHER PUBLICATIONS

Sato et al. Eur. J. Pharmacol. (1982) 83: 91–95.

*Primary Examiner*—Jean C. Witz
*Attorney, Agent, or Firm*—Sughrue, Mion, Zinn, Macpeak & Seas, PLLC

[57] ABSTRACT

This invention relates to an NF-κB activity inhibitor which contains alkaloids originated from a plant belonging to the genus Stephania of the family Menspermaceae, derivatives thereof and salts thereof, as the active components, to an agent for use in the treatment and prevention of diseases upon which the NF-κB activity inhibiting action is effective and to an inhibitor of the expression of related genes. Since said active components exert an action to inhibit transcription of DNA having an NF-κB recognition sequence by inhibiting the activity of NF-κB, the drug of the present invention can inhibit expression of genes of certain substances such as cytokines, inflammatory cytokine receptor antagonists, MHC class I, MHC class II, β2 microglobulin, immunoglobulin light chain, serum amyloid A, angiotensinogen, complement B, complement C4, C-myc gene, HIV, SV40, CMV, adenovirus and the like, so that the inventive drug is useful in treating and/or preventing various diseases in which these substances are taking roles.

6 Claims, No Drawings

NF-ĸB ACTIVITY INHIBITOR

FIELD OF THE INVENTION

This invention relates to an NF-κB activity inhibitor, to agents for use in the treatment and prevention of diseases upon which NF-κB activity inhibiting action is effective, particularly an agent for the treatment and prevention of inflammatory diseases, an agent for the treatment and prevention of autoimmune diseases and an agent for the treatment and prevention of viral diseases, and to a gene expression inhibitor.

BACKGROUND OF THE INVENTION

DNA as the substance of genes is regulated by various factors, and expression of its genetic information is controlled thereby. For example, transcription of genetic information from DNA to RNA is controlled by a plurality of DNA binding proteins which recognizes several to scores of nucleotide sequences on the gene and bind thereto. NF-κB (nuclear factor-κB) known as one of such DNA binding proteins is present in the nuclear extract of B cells which are antibody-producing cells and has been identified as a factor that binds to the enhancer of immunoglobulin κ chain (Igκ) gene. With the progress of studies on this factor, it has been revealed that this is a transcription factor which takes part in the expression induction of a large number of genes that are induced by stimulation and is broadly concerned in the regulation of vital phenomenon.

This NF-κB is generally present in the cytoplasm in the form of a complex in which its homodimer of proteins having a molecular weight of 50 kD or its heterodimer of a protein of 50 kD in molecular weight and a protein of 65 kD in molecular weight is bonded to a protein called I-κB which inhibits activity of the dimer. When a certain stimulation is given to the cells, I-κB is modified and released from the complex to cause activation of NF-κB, so that the dimer is transferred into the nucleus and its DNA binding activity becomes detectable. It is known that this activity is generated as a result of direct activation, not mediated by the expression of other genes such as second messengers and the like.

In addition, the NF-κB binding sequence on DNA has been found in various genes and it has been shown that it is actually important for the expression of the function of genes. The binding sequence of NF-κB (κB motif) is composed of about 10 bases having a common sequence which starts with a cluster of G (guanine) and ends with a cluster of C (cytosine) (consensus sequence 5'-GGGRNNYCCC-3')(SEQ ID NO:1. However, a number of sequences to which DNA binding proteins can be bonded are present on the genes of interleukin-1 (to be referred to as IL-1 hereinafter in some cases) and tumor necrosis factor (to be referred to as TNF hereinafter in some cases) which are known as inflammatory proteins, and it is known that the NF-κB binding sequence is also present therein (Clark, B. D. et al., *Nucl. Acids Res.*, 14, 7898, 1984; Nedospasov, S. A. et al., *Cold Spring Harb. Symp. Quant. Biol.*, 51, 611, 1986). Actually, it has been reported that the binding of NF-κB inhibits transcription to mRNA (Hiscott, J. et al., *Mol. Cell. Biol.*, 13, 6231, 1993; Collart, M. A. et al., *Mol. Cell. Biol.*, 10, 1498, 1990).

As a substance which inhibits the transcription factor of NF-κB, an NF-κB binding protein has been disclosed in European Patent 584238.

In addition, it has been reported that a composition which contains an alkaloid originated from a plant belonging to the genus Stephania of the family Menspermaceae, as its active ingredient, inhibits production of TNFα, interleukin-6 (to be referred to as IL-6 hereinafter in some cases) and interleukin-8 (to be referred to as IL-8 hereinafter in some cases) (JP-A-8-301761, the term "JP-A" as used herein means an "unexamined published Japanese patent application").

Phospholipid which constitutes the biological membrane releases arachidonic acid by the action of phospholipase $A_2$. Leukotriene, thromboxane, prostaglandine and the like are produced from the arachidonic acid by the action of 5-lipoxygenase or cyclooxygenase. These substances exert complex physiological activities and take important roles in the maintenance and regulation of the living body. In the living body, various cytokines are released by receiving various types of stimulation and cause inflammatory reactions. The prior art drugs inhibit expression of histamine and leukotriene B4 or prostaglandine E2 or the like inflammatory protein by the antagonism on mediator receptors of histamine and the like or by the inhibition of lipoxygenase, cyclooxygenase and the like metabolic enzymes in the arachidonic acid cascade. However, effects of non-steroidal drugs are expected for only symptomatic therapy and not sufficient as radical therapy, while steroid drugs are effective but have a problem in that they cannot be administered for a prolonged period of time due to their strong side effects. Particularly, autoimmune disease and the like inflammatory diseases become chronic in many cases and therefore require prolonged medical treatments, so that drugs having side effects are not applicable to such diseases. In addition, NF-κB takes an important role in the replication of HIV-1, so that search for a substance capable of inhibiting NF-κB activity is expected for not only its anti-inflammatory effects but also inhibition of acquired immunodeficiency syndrome (AIDS and the like) by its effect to inhibit transcription of long terminal repeat (LTR) of HIV-1, namely replication of the virus.

SUMMARY OF THE INVENTION

In view of the above, it therefore becomes an object of the present invention to provide an NF-κB activity inhibitor. Another object of the present invention is to provide an agent for the treatment and prevention of diseases upon which NF-κB activity inhibiting action is effective. Sill another object of the present invention is to provide an inhibitor of the expression of genes based on the NF-κB activity inhibiting action.

The inventors of the present invention have conducted intensive studies on the methods and substances which can radically inhibit various inflammatory cytokines and found as the results that alkaloids originated from a plant belonging to the genus Stephania of the family Menspermaceae, derivatives thereof and salts thereof can inhibit various cytokines and the like at the gene level based on their transcription factor NF-κB activity inhibiting action and have an activity to inhibit transcription of HIV-1 LTR. The present invention has been accomplished on the basis of these findings.

Accordingly, the present invention relates to an NF-κB activity inhibitor which comprises, as its active ingredient, at least one compound selected from the group consisting of alkaloids originated from a plant belonging to the genus Stephania of the family Menspermaceae, derivatives thereof and salts thereof; to an agent for the treatment and prevention of diseases upon which NF-κB activity inhibiting action is effective (particularly an agent for the treatment and prevention of inflammatory diseases, an agent for the treatment and prevention of autoimmune diseases and an agent for the treatment and prevention of viral diseases); and to an gene expression inhibitor.

The present invention also relates to a method for inhibiting NF-κB activity which comprises using at least one compound selected from the group consisting of alkaloids originated from a plant belonging to the genus Stephania of the family Menspermaceae, derivatives thereof and salts thereof; to a method for the treatment and prevention of diseases upon which NF-κB activity inhibiting action is effective (particularly for the treatment and prevention of inflammatory diseases, for the treatment and prevention of autoimmune diseases and or the treatment and prevention of viral diseases); and to a method for inhibiting expression of genes.

Moreover, the present invention relates to use of at least one compound selected from the group consisting of alkaloids originated from a plant belonging to the genus Stephania of the family Menspermaceae, derivatives thereof and salts thereof, for the manufacture of an NF-κB activity inhibitor; use thereof for the manufacture of an agent for the treatment and prevention of diseases upon which NF-κB activity inhibiting action is effective (particularly an agent for the treatment and prevention of inflammatory diseases, an agent for the treatment and prevention of autoimmune diseases and an agent for the treatment and prevention of viral diseases); and to use thereof for the manufacture of an gene expression inhibitor.

DETAILED DESCRIPTION OF THE INVENTION

The alkaloid as the active ingredient of the present invention can be extracted in the usual way from a plant belonging to the genus Stephania of the family Menspermaceae (for example, *Stephania cepharantha* Hayata, *Stephania sasaki* Hayata or the like). Preferably, the alkaloid originated from *Stephania cepharantha* Hayata is used.

An extract obtained by concentrating the extract from a plant belonging to the genus Stephania, a precipitate which is formed when an acidic solution of the extract is alkalified and an alkaloid-containing fraction separated by this treatment, as well as crystals obtained by separating and purifying the alkaloid in the usual way and derivatives of said alkaloid produced known methods, can be used as the active ingredient of the present invention. For example, an alkaloid fraction can be separated by extracting a plant of the genus Stephania (its roots, stems, seeds, leaves and the like can be used, though not particularly limited to these parts) with methanol, ethanol, acetone, ethyl acetate, benzene or the like solvent, concentrating the extract, dissolving the concentrate in dilute hydrochloric acid, dilute sulfuric acid, citric acid aqueous solution, oxalic acid aqueous solution or the like acidic solution, alkalifying the solution and then collecting the thus formed precipitate. The thus obtained fraction may be further purified by various chromatography techniques, recrystallization and the like known means.

Examples of the alkaloid originated from a plant of the genus Stephania include cepharanthine, isotetrandrine, berbamine, cycleanine, homoaromoline, cepharanoline, aromoline, obamegine, norcycleanine, 2-norcepharanthine, 2-norcepharanoline, 2-norberbamine, secocepharanthine, obaberine, 2-norisotetrandrine, oxyacanthine, stephibaberine, thalrugosine and the like bisbenzylisoquinoline alkaloids; coclaurine, reticuline, laudanidine, protosinomenine, N-methylcoclaurine and the like benzyl-isoquinoline alkaloids; FK-3000, sinomenine, cephamonine, tannagine, cephamuline and the like morphinan alkaloids; lastourvilline, isocorydine, corydine and the like aporphine alkaloids; stepharine and the like proaporphine alkaloids; and cepharamine, aknadinine, aknadilactam and the like hasubanane alkaloids.

Examples of the aforementioned derivatives of said alkaloid include acyl derivatives, alkyl derivatives, carbamoyl derivatives and the like.

Examples of the acyl group in the acyl derivatives include saturated straight chain aliphatic acyl groups having 2 to 18 carbon atoms (for example, acetyl, propionyl, butyryl, valeryl, caproyl, capryloyl, lauroyl, palmitoyl, stearoyl and the like groups), aromatic acyl groups (for example, benzoyl, 4-methoxybenzoyl, 4-chlorobenzoyl, 4-nitrobenzoyl, 3,4-dimethoxybenzoyl, 1-naphthalenecarboxy, 3-indolecarboxy and the like groups) and aryl acetate groups (for example, phenylacetyl, 4-methoxyphenylacetyl, 4-chlorophenylacetyl, 4-nitrophenylacetyl, 3,4-dimethoxyphenylacetyl, 1-naphthaleneacetyl, 3-indoleacetyl and the like groups).

Illustrative examples of the acyl derivatives include
12-O-acetylcepharanoline, 12-9-propionylcepharanoline,
12-O-butyrylcepharanoline, 12-O-valerylcepharanoline,
12-O-caproylcepharanoline, 12-O-capryloylcepharanoline,
12-O-lauroylcepharanoline, 12-O-palmitoylcepharanoline,
12-O-stearoylcepharanoline, 12-O-benzoylcepharanoline,
12-O-(4-methoxybenzoyl)cepharanoline,
12-O-(4-chlorobenzoyl)cepharanoline,
12-O-(4-nitrobenzoyl)cepharanoline,
12-O-(3,4-dimethoxybenzoyl)cepharanoline,
12-O-(1-naphthalenecarboxy)cepharanoline,
12-O-(3-indolecarboxy)cepharanoline,
12-O-phenylacetylcepharanoline,
12-O-(4-methoxyphenyl)acetylcepharanoline,
12-O-(4-chlorophenyl)acetylcepharanoline,
12-O-(4-nitrophenyl)acetylcepharanoline,
12-O-(3,4-dimethoxyphenyl)acetylcepharanoline,
12-O-(1-naphthalene)acetylcepharanoline,
12-O-(3-indole)acetylcepharanoline and the like.

Examples of the alkyl group in the alkyl derivatives include methyl, ethyl, propyl, butyl, pentyl, hexyl, heptyl, octyl, nonyl, decyl, undecyl and the like saturated straight chain alkyl groups having 1 to 11 carbon atoms, as well as benzyl, 3-methoxybenzyl, 3-chlorobenzyl, 1-naphthalenemethyl and the like groups.

Illustrative examples of the alkyl derivatives include
12-O-methylcepharanoline, 12-O-ethylcepharanoline,
12-O-propylcepharanoline, 12-O-butylcepharanoline,
12-O-pentylcepharanoline, 12-O-hexylcepharanoline,
12-O-heptylcepharanoline, 12-O-octylcepharanoline,
12-O-nonylcepharanoline, 12-O-decylcepharanoline,
12-O-undecylcepharanoline, 12-O-benzylcepharanoline,
12-O-(3-methoxybenzyl)cepharanoline,
12-O-(3-chlorobenzyl)cepharanoline,
12-O-(1-naphthalenemethyl)cepharanoline and the like.

The carbamoyl derivatives may have a (mono or di)alkyl substituted carbamoyl group, and examples of the alkyl group as a substituent group include those which are described above, as well as cyclohexyl, benzyl, 4-methoxybenzyl, 4-chlorobenzyl, furfuryl and the like groups.

Illustrative examples of the carbamoyl derivatives include
12-O-ethylcarbamoylcepharanoline,
12-O-propylcarbamoylcepharanoline,
12-O-butylcarbamoylcepharanoline,
12-O-pentylcarbamoylcepharanoline, 12-O-hexylcarbamoylcepharanoline,
12-O-heptylcarbamoylcepharanoline,
12-O-octylcarbamoylcepharanoline,
12-O-nonylcarbamoylcepharanoline,
12-O-decylcarbamoylcepharanoline,
12-O-cyclohexylcarbamoylcepharanoline,
12-O-benzylcarbamoylcepharanoline,
12-O-(4-methoxybenzyl)carbamoylcepharanoline,
12-O-(4-chlorobenzyl)carbamoylcepharanoline,
12-O-furfurylcarbamoylcepharanoline,
12-O-diethylcarbamoylcepharanoline,
12-O-dipropylcarbamoylcepharanoline,
12-O-dibutylcarbamoylcepharanoline,
12-O-dihexylcarbamoylcepharanoline,
12-O-dioctylcarbamoylcepharanoline,
12-O-didecylcarbamoylcepharanoline and the like.

The NF-κB activity inhibitor, agent for the treatment and prevention of diseases upon which the NF-κB activity inhibiting action is effective and inhibitor of the expression of genes of the present invention may contain at least one alkaloid, a derivative thereof or a salt thereof or may contain a mixture of two or more alkaloids, derivatives thereof or salts thereof.

The aforementioned bisbenzylisoquinoline alkaloids are compounds having the following structures.

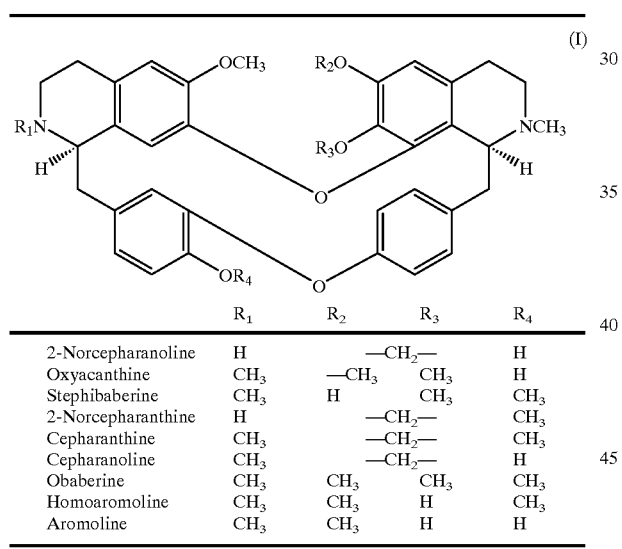

(I)

|  | $R_1$ | $R_2$ | $R_3$ | $R_4$ |
|---|---|---|---|---|
| 2-Norcepharanoline | H | —$CH_2$— | | H |
| Oxyacanthine | $CH_3$ | —$CH_3$ | $CH_3$ | H |
| Stephibaberine | $CH_3$ | H | $CH_3$ | $CH_3$ |
| 2-Norcepharanthine | H | —$CH_2$— | | $CH_3$ |
| Cepharanthine | $CH_3$ | —$CH_2$— | | $CH_3$ |
| Cepharanoline | $CH_3$ | —$CH_2$— | | H |
| Obaberine | $CH_3$ | $CH_3$ | $CH_3$ | $CH_3$ |
| Homoaromoline | $CH_3$ | $CH_3$ | H | $CH_3$ |
| Aromoline | $CH_3$ | $CH_3$ | H | H |

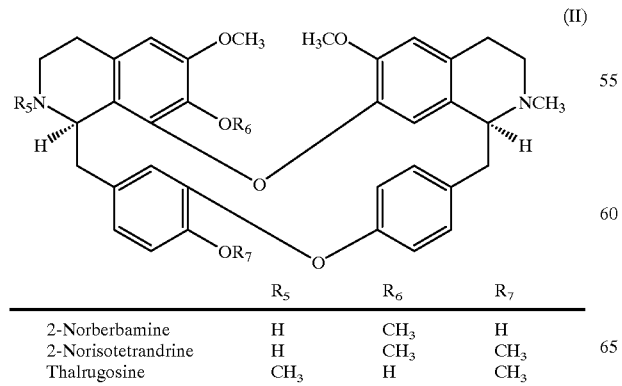

(II)

|  | $R_5$ | $R_6$ | $R_7$ |
|---|---|---|---|
| 2-Norberbamine | H | $CH_3$ | H |
| 2-Norisotetrandrine | H | $CH_3$ | $CH_3$ |
| Thalrugosine | $CH_3$ | H | $CH_3$ |

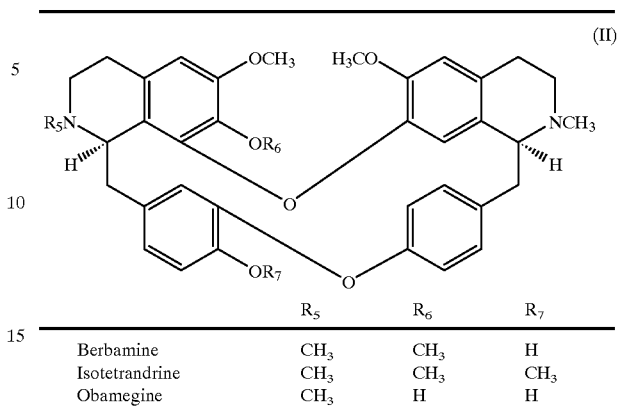

(II)

|  | $R_5$ | $R_6$ | $R_7$ |
|---|---|---|---|
| Berbamine | $CH_3$ | $CH_3$ | H |
| Isotetrandrine | $CH_3$ | $CH_3$ | $CH_3$ |
| Obamegine | $CH_3$ | H | H |

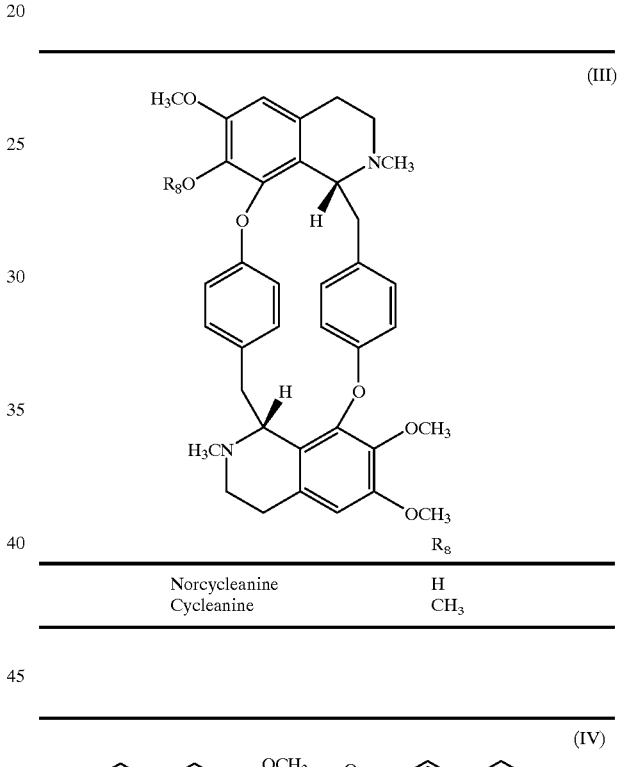

(III)

|  | $R_8$ |
|---|---|
| Norcycleanine | H |
| Cycleanine | $CH_3$ |

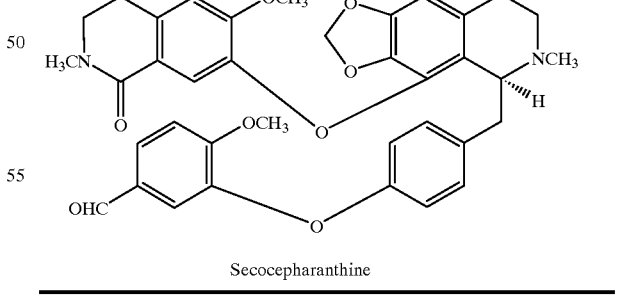

(IV)

Secocepharanthine

Also, the aforementioned benzylisoquinoline alkaloids are compounds having the following structures.

(V)

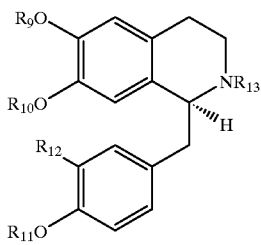

|               | $R_9$  | $R_{10}$ | $R_{11}$ | $R_{12}$ | $R_{13}$ |
|---------------|--------|----------|----------|----------|----------|
| Protosinomenine | H    | $CH_3$   | $CH_3$   | OH       | $CH_3$   |
| N-Methylcoclaurine | $CH_3$ | H    | H        | H        | $CH_3$   |
| Reticuline    | $CH_3$ | H        | $CH_3$   | OH       | $CH_3$   |
| Coclaurine    | $CH_3$ | H        | H        | H        | H        |
| Laudanidine   | $CH_3$ | $CH_3$   | $CH_3$   | OH       | $CH_3$   |

The NF-κB activity inhibitor, agent for the treatment and prevention of diseases upon which the NF-κB activity inhibiting action is effective and inhibitor of the expression of genes of the present invention may preferably contain at least one alkaloid selected from cepharanthine, isotetrandrine, berbamine, cycleanine, homoaromoline and cepharanoline, of which cepharanthine is more preferred.

The alkaloid or a derivative thereof may be in the form of a salt, particularly a pharmaceutically acceptable salt such as an acid addition salt. Examples of the pharmaceutically acceptable salt include addition salts of hydrochloric acid, hydrobromic acid, sulfuric acid, phosphoric acid, nitric acid and the like inorganic acids and addition salts of acetic acid, succinic acid, malic acid, tartaric acid, citric acid, maleic acid, fumaric acid, methanesulfonic acid, p-toluenesulfonic acid and the like organic acids.

As a pharmaceutical preparation which contains alkaloids originated from a plant of the genus Stephania, Cepharanthin (registered trademark by Kaken Shoyaku Co., Ltd.) is already on the market as a preparation of alkaloids extracted from *Stephania cepharantha* Hayata.

Cepharanthin (registered trademark) contains cepharanthine, isotetrandrine, berbamine, cycleanine, homoaromoline, cepharanoline, aromoline, obamegine, norcycleanine, 2-norcepharanthine, 2-norcepharanoline, 2-norberbamine, secocepharanthine, obaberine, 2-norisotetrandrine, oxyacanthine and thalrugosine as alkaloids. Among these alkaloids, main alkaloid components of Cepharanthin (registered trademark) are cepharanthine, isotetrandrine, berbamine, cycleanine, homoaromoline and cepharanoline.

According to the present invention, the term "Cepharanthin (registered trademark)" means a pharmaceutical preparation of alkaloids extracted from *Stephania cepharantha* Hayata, which is an article on the market (available from Kaken Shoyaku Co., Ltd.), and the term "cepharanthine" means an alkaloid of the aforementioned structural formula (I) (in the formula, $R_1$ is $CH_3$, $R_2$ and $R_3$ form —$CH_2$— and $R_4$ is $CH_3$).

The alkaloids originated from a plant belonging to the genus Stephania of the family Menspermaceae, derivatives thereof and salts thereof, as the active ingredient of the present invention, inhibit transcription of DNA having an NF-κB recognition sequence by inhibiting activity of the transcription factor NF-κB. Thus, said active ingredient can inhibit expression of corresponding protein of a gene effectively, if the gene has the NF-κB recognition sequence. In consequence, the NF-κB activity inhibitor, agent for the treatment and prevention of diseases upon which the NF-κB activity inhibiting action is effective and gene expression inhibitor of the present invention, which contain said active ingredient, can inhibit expression of genes of cytokines such as IL-1 and TNF, as well as interleukin-2 (to be referred to as IL-2 hereinafter in some cases), IL-6, IL-8, granulocyte colony stimulating factor (to be referred to as G-CSF hereinafter in some cases), interferon β (to be referred to as IFN-β hereinafter in some cases) and the like, genes of receptor antagonists of inflammatory cytokines such as interleukin-1 receptor antagonist (to be referred to as IL-IRA hereinafter in some cases) and the like, genes of major histocompatibility antigen (to be referred to as MHC hereinafter in some cases) class I, MHC class II, β2 microglobulin, immunoglobulin light chain, serum amyloid A, angiotensinogen, complement B, complement C4 and the like, C-myc gene which is one of oncogenes and genes of viruses such as human immunodeficiency virus (to be referred to as HIV hereinafter in some cases), simian virus 40 (to be referred to as SV40 hereinafter in some cases), cytomegalovirus (to be referred to as CMV hereinafter in some cases), adenovirus and the like, so that these activity inhibitor, therapeutic and preventive agent and expression inhibitor can prevent and treat diseases in which such genes are concerned and are particularly useful in preventing and treating inflammatory diseases, autoimmune diseases and viral diseases.

That is, the drug of the present invention is effective for the treatment and prevention of diseases such as rheumatoid arthritis, systemic lupus erythematosus, systemic scleroderma, Behcet disease, periarteritis, ulcerative colitis, Crohn disease, active chronic hepatitis, glomerular nephritis and the like various autoimmune diseases; and osteoarthritis, gout, atherosclerosis, psoriasis, atopic dermatitis, pulmonary diseases with granuloma, various intractable diseases in which inflammatory symptoms such as of various types of encephalitis are the basis of the morbid state, endotoxin shock, sepsis, inflammatory colitis, diabetes, acute myelocytic leukemia, pneumonia, heart transplantation, encephalomylitis, anorexia, acute hepatitis, chronic hepatitis, drug induced hepatic injury, alcoholic hepatitis, viral hepatitis, jaundice, hepatic cirrhosis, hepatic insufficiency, atrial myxoma, Castleman syndrome, multiple myeloma, Rennert T lymphomatosis, mesangial nephritis, renal cell carcinoma, cytomegaloviral hepatitis, cytomegaloviral retinopathy, adenoviral cold syndrome, adenoviral pharyngoconjunctival fever, adenoviral ophthalmia, AIDS and the like.

When the drug of the present invention is administered, said active ingredient may be used directly or by oral administration after making it into tablets, powders, granules, capsules, syrups and the like dosage forms, or by parenteral administration after making it into suppositories, injections, external preparations, drip infusions and the like dosage forms, but it is desirable to administer it as oral administration preparations.

Pharmaceutical preparations for use in the oral or parenteral administration are produced in the usual way using common pharmaceutically acceptable carriers. For example, when a solid preparation for oral administration use is prepared, the principal agent is mixed with a filler and, as occasion demands, a binder, a disintegrator, a lubricant, a coloring agent, a corrective and the like and then the mixture is made into tablets, coated tablets, granules, powders, capsules and the like forms. Lactose, corn starch, sucrose, glucose, sorbitol, crystalline cellulose, silicon dioxide or the like can be used as the filler, polyvinyl alcohol, polyvinyl ether, ethyl cellulose, methyl cellulose, acacia, tragacanth, gelatin, shellac, hydroxypropyl cellulose, hydroxypropylmethyl cellulose, calcium citrate, dextrin, pectin or the like can be used as the binder, magnesium stearate, talc, polyethylene glycol, silica, hardened plant oil or the like can be used as the lubricant, pharmaceutically acceptable coloring agent can be used as the coloring agent, and cocoa powder, mentha water, aromatic acid, mentha oil, borneol, powdered cinnamon bark or the like can be used as the corrective. As a matter of course, these tablets and granules can be coated by sugar coating, gelatin coating and the like optional means as occasion demands. If necessary, an antiseptic agent, an antioxidant and the like may be added.

When injections, drip infusions and the like are prepared, a pH adjusting agent, a buffer, a stabilizer, a solubilizing agent and the like may be added to the principal agent and, after carrying out freeze drying or the like treatment as occasion demands, the mixture is made into injections or drip infusions for subcutaneous, intramuscular or intravenous administration use.

The subject of the present invention is vertebrates, preferably mammals, and more preferably human.

Dosage of the drug of the present invention varies depending on the kind of the disease, degree of the symptoms, age of the patient and the like conditions, but, when the drug is administered to human in the form of an oral preparation for example, it may be administered at a daily dose of generally from 0.02 to 20 mg/kg, preferably from 0.1 to 10 mg/kg, more preferably from 0.2 to 6 mg/kg, as said alkaloid, a derivative thereof or a salt thereof, by dividing the daily dose into 1 to several doses per day.

Since the active ingredient according to the present invention can inhibit NF-κB activity and also can inhibit expression of certain genes, for example, those having the NF-κB binding sequence (especially, the genes in which NF-κB is highly participated in their expression, such as HIV and TNF-α), it is apparent for one skilled in the art that the agents according to the present invention are useful in various in vitro, in vivo, ex vivo and other studies and experiments.

EXAMPLES

Examples of the present invention are given below by way of illustration and not by way of limitation.

Test Example 1
Inhibition Action on NF-κB Binding Activation

In order to examine the action of a test compound cepharanthine to inhibit NF-κB binding activation, U1 [a cell strain derived from HIV-1 (HIV type 1) latent infection human monocyte] cells were stimulated or not stimulated with phorbol 12-myristate 13-acetate (PMA) in the presence or absence of the test compound, and the following assay was carried out using a nucleoprotein extract obtained from the resulting cells.
[Gel shift assay]

Gel shift assay was carried out using an NF-κB probe of HIV-1. A double-stranded DNA fragment of an NF-κB site-like sequence, 5'-AGT TGA GGG GAC TTT CCC AGG C-3' from the transcription initiation point, was used as the NF-κB probe of HIV-1. The 5'-terminus of the probe was radiation-labeled with $^{32}$p in the usual way using [γ-$^{32}$P]ATP and polynucleotide kinase. In an ice bath, 10 μg of the nucleoprotein extract obtained in the above was mixed with a binding buffer [20 mM Hepes, pH 7.9/0.1 M KCl/0.5 mM dithiothreitol (DTT)/0.2 mM ethylenediaminetetraacetic acid (EDTA)/0.5 mM phenylmethylsulfonyl fluoride (PMSP)/20% glycerol] and, in order to detect only of the activity of the protein of interest in the nucleoprotein extract, further with DNA (carrier) poly(d1-dC) to which the protein of interest does not bind, and the resulting mixture was allowed to undergo 5 minutes of the reaction at room temperature. At the same time, a sample in which a large quantity of non-labeled probe was added to the reaction solution was prepared and the same reaction was carried out as a competitive assay. Thereafter, the $^{32}$P-labeled NF-κB probe was added thereto to carry out 20 minutes of binding reaction at room temperature. After the reaction, 4% unmodified polyacrylamide gel electrophoresis was carried out in order to separate the DNA-NF-κB complex from free oligonucleotide. The gel was subjected to autoradiography, and NF-κB in the nucleoprotein extract was determined by an image analyzer (BIO-RAD, Model GS-700 Imaging Densitometer).

The action of the test compound to inhibit activation of NF-κB binding by PMA stimulation of U1 cells (inhibition ratio, %) is shown in Table 1.

TABLE 1

|    | Average (OD) | Area (mm × mm) | Labeled amount (OD × mm × mm) | % Inhibition |
|----|--------------|----------------|-------------------------------|--------------|
| V1 | 0.377        | 65.54          | 24.71                         | (—)          |
| V2 | 0.473        | 74.85          | 35.40                         | —            |
| V3 | 0.447        | 70.53          | 31.53                         | 10.9*        |
| V4 | 0.442        | 69.15          | 30.56                         | 13.7*        |
| V5 | 0.548        | 83.83          | 45.94                         | —            |
| V6 | 0.491        | 70.45          | 34.59                         | 24.7**       |
| V7 | 0.490        | 50.63          | 24.81                         | 46.0**       |
| V8 | 0.377        | 54.39          | 20.51                         | 55.4**       |
| V9 | 0.447        | 80.61          | 36.03                         | 21.6**       |

V1: Negative control (nucleoprotein extract not contained)
V2: Control (nucleoprotein extract of untreated U1 cells)
V3: Cepharanthine control; reaction (2.5 hours) of U1 cells in the presence of 0.1 μg/ml of cepharanthine
V4: Cepharanthine control; reaction (2.5 hours) of U1 cells in the presence of 1 μg/ml of cepharanthine
V5: Stimulation (0.5 hour) of U1 cells with 10 ng/ml of PMA
V6: Reaction (2 hours) of U1 cells in the presence of 0.1 μg/ml of cepharanthine + stimulation (0.5 hour) with 10 ng/ml of PMA
V7: Reaction (2 hours) of U1 cells in the presence of 1 μg/ml of cepharanthine + stimulation (0.5 hour) with 10 ng/ml of PMA
V8: (Competitive assay) V5 + competitive NF-κB cold probe
V9: (Competitive assay) V5 + noncompetitive SP1 cold probe
*: V3 and V4 vs. V2,
**: V6, V7, V8 and V9 vs. V5

The above results show that the drug of the present invention has significant effect to inhibit NF-κB binding activation.

Test Example 2
Inhibition action on HIV-1 LTR transcription activity

In order to examine effect of a test compound cepharanthine on the HIV-1 transcription activity, CAT assay was carried out by the following method.
[HIV-1 LTR CAT assay]

A plasmid in which chloramphenicol acetyltransferase (CAT) gene has been linked to the downstream of HIV-1 LTR gene was introduced by lipofection into HeLa cells adjusted to a density of 1×10$^6$ cells, and the resulting cells were cultured in the presence or absence of the test compound and phorbol 12-myristate 13-acetate (PMA). After 48 hours of the culturing, the cells were collected and washed to prepare a cell extract using a freeze-thawing method. The thus prepared cell extract was allowed to react with acetyl CoA and [$^{14}$C]-labeled chloramphenicol (CM), and the thus formed acetyl[$^{14}$C]CM was separated by a thin layer chromatography, subjected to autoradiography and then qualitatively measured using an image analyzer (BIO-RAD, Model GS-700 Imaging Densitometer). Inhibition ratio based on the labeled amount obtained in the absence of the test compound is shown in Table 2.

TABLE 2

|    | Average (OD) | Area (mm × mm) | Labeled amount (OD × mm × mm) | % Inhibition |
|----|--------------|----------------|-------------------------------|--------------|
| V1 | 0.703 | 59.93 | 42.13 | (—) |
| V2 | 0.905 | 72.02 | 65.18 | (—) |
| V3 | 0.892 | 81.14 | 72.38 | — |
| V4 | 0.892 | 54.31 | 48.44 | 33.1* |
| V5 | 0.867 | 41.00 | 35.55 | 50.9* |

V1: Negative control
V2: Plasmid control
V3: HeLa cells were cultured in the presence of PMA (10 ng/ml)
V4: HeLa cells were cultured in the presence of cepharanthine (0.1 μg/ml) + PMA (10 ng/ml)
V5: HeLa cells were cultured in the presence of cepharanthine (1 μg/ml) + PMA (10 ng/ml)
*: V4 and V5 vs. V3

The above results show that the drug of the present invention has significant effect to inhibit HIV-1 LTR transcription activity.

Test Example 3
Acute Toxicity Test

The $LD_{50}$ values (mg/kg) in an acute toxicity test carried out using male mice are shown in Table 3.

TABLE 3

| Route of administration | Drugs tested | $LD_{50}$ (mg/kg) |
|---|---|---|
| Oral | Cepharanthin (registered trademark) | 1900 |
|  | cepharanthine | 3410 |
| Intravenous | Cepharanthin (registered trademark) | 45 |
|  | cepharanthine | 47.0 |
|  | berbamine | 18.8 |
|  | isotetrandrine | 32.5 |
|  | cycleanine | 62.5 |
|  | homoaromoline | 42.4 |
|  | cepharanoline | 34.3 |

Formulation Example 1

A 500 mg portion of cepharanthine hydrochloride was thoroughly mixed with 3.0 g of lactose, 1.28 g of corn starch, 200 mg of hydroxypropyl cellulose and 20 mg of magnesium stearate, and the mixture was granulated and then made into tablets, thereby obtaining tablets of 100 mg per tablet.

Formulation Example 2

A 500 mg portion of an alkaloid fraction of *Stephania sasaki* Hayata was thoroughly mixed with 2.5 g of lactose, 1.75 g of potato starch, 240 mg of-crystalline cellulose and 10 mg of calcium stearate, and the mixture was packed into capsules to prepare capsules each capsule containing 10 mg of alkaloid components.

Formulation Example 3

A 500 mg portion of an alkaloid fraction of *Stephania cepharantha* Hayata was dissolved in dilute hydrochloric acid, and the solution was mixed with distilled water for injection use, isotonized with sodium chloride and then filled up to a total volume of 100 ml. Thereafter, the resulting solution was filtered through a 0.2 g membrane filter, dispensed and heat-sealed into 10 ml capacity ampoules and then heat-sterilized to obtain injections.

Production Example Production of Cepharanthin (registered trademark)

A methanol extract of tuberous roots of *Stephania cepharantha* Hayata belonging to the genus Stephania of the family Menspermaceae was dissolved in dilute hydrochloric acid, the resulting solution was alkalified with sodium hydroxide and then-the thus formed precipitate was collected by filtration. The thus obtained precipitate was washed with dilute sodium hydroxide aqueous solution and extracted with ether, and then the resulting extract was concentrated under a reduced pressure to obtain the title product.

As has been described in the foregoing, the alkaloids originated from a plant belonging to the genus Stephania of the family Menspermaceae, derivatives thereof and salts thereof, as the active components of the present invention, exert an action to inhibit transcription of DNA having an NF-κB recognition sequence by inhibiting the activity of the transcription factor NF-κB. Because of this, the drug of the present invention which contains the just described active components can inhibit expression of genes of certain substances such as IL-1, TNF, IL-2, IL-6, IL-8, G-CSF, IFN-β and the like cytokines and IL-IRA and the like inflammatory cytokine receptor antagonists, as well as MHC class I, MHC class II, β2 microglobulin, immunoglobulin light chain, serum amyloid A, angiotensinogen, complement B, complement C4, C-myc gene, HIV, SV40, CMV, adenovirus and the like, so that the inventive drug is useful in treating and/or preventing various diseases, particularly inflammatory diseases, autoimmune diseases and viral diseases, in which these substances are taking roles.

While the invention has been described in detail and with reference to specific embodiments thereof, it will be apparent to one skilled in the art that various changes and modifications can be made therein without departing from the spirit and scope thereof.

What is claimed is:

1. A method for inhibiting NF-κB activity in a vertebrate which comprises administering to a vertebrate in need of treatment, a therapeutically effective amount of at least one compound selected from the group consisting of alkaloids obtainable from a plant belonging to the genus Stephania of the family Menspermaceae, derivatives thereof, and pharmaceutically acceptable salts thereof, provided that the compound is not cepharanthine.

2. The method according to claim 1, wherein the plant belonging to the genus Stephania is *Stephania cepharantha* Hayata.

3. The method according to claim 1, wherein the derivatives are acyl, alkyl or carbamoyl derivatives of the at least one compound.

4. A method for inhibiting NF-κB activity in a vertebrate which comprises administering to a vertebrate in need of treatment, a therapeutically effective amount of at least one compound selected from the group consisting of isotetrandrine, berbamine, cycleanine, homoaromoline, cepharanoline, aromoline, obamegine, norcycleanine, 2-norcepharanthine, 2-norcepharanoline, 2-norberbamine, secocepharanthine, obaberine, 2-norisotetrandrine, oxyacanthine, stephibaberine, thalrugosine, coclaurine, reticuline, laudanidine, protosinomenine, N-methylcoclaurine, FK-3000, sinomenine, cephamonine, tannagine, cephamuline, lastourvilline, isocorydine, corydine, stepharine, cepharamine, aknadinine and aknadilactam, derivatives thereof, and pharmaceutically acceptable salts thereof, provided that the compound is not cepharanthine.

5. The method according to claim 4, wherein the compound is at least one member selected from the group consisting of isotetrandrine, berbamine, cycleanine, homoaromoline and cepharanoline.

6. The method according to claim 4, wherein the derivatives are acyl, alkyl or carbamoyl derivatives of the at least one compound.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 10 base pairs
      (B) TYPE: nucleic acid -continued

```
        (C) STRANDEDNESS: single
        (D) TOPOLOGY: linear (ii) MOLECULE TYPE: DNA (genomic)

(xi) SEQUENCE DESCRIPTION: SEQ ID NO:1:

GGGRNNYCCC                                                                10

(2) INFORMATION FOR SEQ ID NO:2:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:2:

AGTTGAGGGG ACTTTCCCAG GC                                                  22
```